United States Patent [19]

Takeda et al.

[11] Patent Number: 5,094,846
[45] Date of Patent: Mar. 10, 1992

[54] TRIOXANE COMPOSITION AND INSECT-PROOFING AGENT

[75] Inventors: Mutsuhiko Takeda, Tokyo; Minoru Kakuda, Matsudo; Masafumi Shimpo, Kashiwa; Kiyoshi Yoshida, Tokyo, all of Japan

[73] Assignee: Mitsubishi Gas Chemical Co., Inc., Tokyo, Japan

[21] Appl. No.: 554,383

[22] Filed: Jul. 19, 1990

[30] Foreign Application Priority Data

Jul. 21, 1989 [JP] Japan .................................. 1-190200

[51] Int. Cl.$^5$ ...................... A01N 43/32; A61K 31/74
[52] U.S. Cl. .................................... 514/452; 514/407; 514/409; 252/182.23
[58] Field of Search ................ 514/452; 424/407, 409, 424/452, 78

[56] References Cited

U.S. PATENT DOCUMENTS

| | | | |
|---|---|---|---|
| 3,097,129 | 7/1963 | Laffetay et al. | 424/76.3 |
| 4,045,551 | 8/1977 | Ueno et al. | 424/76 |
| 4,763,448 | 5/1988 | Bahadir et al. | 424/409 |
| 4,863,718 | 9/1989 | Bernardo | 424/409 |

OTHER PUBLICATIONS

Chem. Abstracts, vol. 96:117605z.

*Primary Examiner*—Thurman K. Page
*Assistant Examiner*—Peter F. Kulkosky

[57] ABSTRACT

By incorporating a liquid or solid silicone or paraffin into 1,3,5-trioxane, agglomeration of trioxane particles and adhesion of the trioxane to a machine wall or the like can be prevented. The silicone or paraffin is used in an amount of 0.003 to 1% by weight.

7 Claims, No Drawings

TRIOXANE COMPOSITION AND INSECT-PROOFING AGENT

BACKGROUND OF THE INVENTION (1) Field of the Invention

The present invention relates to a 1,3,5-trioxane composition. More particularly, the present invention relates to a 1,3,5-trioxane composition which can be advantageously used as an insect-proofing agent and a starting material for the production of industrial chemicals.

(2) Description of the Related Art 1,3,5-Trioxane (sometimes referred to as "trioxane" hereinafter) is an important substance which is widely used on an industrial scale not only as an insect-proofing agent but also as a starting material for the production of a polyacetal resin and a starting material for the organic synthesis.

In general, flaky or powdery solid trioxane is defective in that flakes or particles are agglomerated in a vessel during the storage to cause caking and form large masses and re-pulverization should be performed when the trioxane is supplied to various molding steps or is transferred. Furthermore, when powdery solid trioxane is molded into tablets, the trioxane adheres to a mortar and a pestle to reduce the operation efficiency.

SUMMARY OF THE INVENTION

We made research with a view to developing an additive to trioxane, capable of solving the above-mentioned problem of caking or adhesion of trioxane, and as the result, it was found that this problem can be solved by adding a silicone or paraffin to trioxane. We have now completed the present invention based on this finding.

More specifically, in accordance with the present invention, there is provided a 1,3,5-trioxane composition comprising 1,3,5-trioxane and a silicone or paraffin.

DETAILED DESCRIPTION OF THE PREFERRED EMBODIMENTS

The silicone used herein is a generic term for a polysiloxane, and the silicone used in the present invention includes a silicone oil which is liquid at room temperature and a silicone resin which is solid at room temperature.

As the liquid silicone oil, there can be mentioned silicone oils composed mainly of a linear polydialkylsiloxane, a linear polyalkylarylsiloxane or a cyclic polydialkylsiloxane, and any of these silicone oils can be used. As preferred examples of the silicone oil, there can be mentioned dimethylpolysiloxane and methylphenylpolysiloxane. Among these silicon oils, a silicone oil having a viscosity of 1 to 10,000 cSt (as measured at 25° C.) is preferably used.

When the composition is used as a volatile insect-proofing agent, a highly volatile silicone oil composed of a cyclopolysiloxane having 3 to 5 siloxane recurring units, such as octamethylcyclotetrasiloxane or decamethylcyclopentasiloxane, is especially preferably used because the silicone oil is not left as a residue after sublimation of trioxane.

Furthermore, a lowly volatile silicone oil having a viscosity of 50 to 1,000 cSt (as measured at 25° C.), such as a linear methylphenylsilicone oil, and a powdery silicone resin, can also be preferably used, because the effect of preventing caking or adhesion in the composition is exerted for a long time.

Any of aliphatic hydrocarbons can be used as the paraffin without any limitation in the present invention. Saturated aliphatic hydrocarbons which are liquid at room temperature, for example, linear saturated aliphatic hydrocarbons represented by the molecular formula of $H_3C(CH_2)_nCH_3$ (in which n is from 6 to 16), are preferably used as the paraffin. Furthermore, a mixture of saturated aliphatic hydrocarbons, such as a liquid paraffin (liquid petrolatum), and a powdery solid paraffin can be preferably used.

Among these paraffins, n-tetradecane, n-pentadecane, n-hexadecane and a liquid paraffin are especially preferably used because the handling is easy and the effect of preventing caking or adhesion in the composition is maintained for a long time.

In the composition of the present invention, the content of the silicone or paraffin is preferably 0.003 to 1% by weight and especially preferably 0.01 to 0.3% by weight. If the content of the silicone or paraffin is lower than 0.003% by weight, the effect of preventing caking or adhesion of trioxane is insufficient. If the content of the silicone or paraffin is within the above-mentioned range, satisfactory results can be obtained, and the silicone or paraffin need not be used in an amount larger than 1% by weight. However, use of the silicone or paraffin in a larger amount is not precluded.

The method for adding the silicone or paraffin used in the present invention is not particularly critical. For example, the silicone or paraffin can be added to trioxane in the melted state.

Especially in the case where a liquid silicone oil or liquid state paraffin is used, there is preferably adopted a method the liquid silicone oil or liquid state paraffin is directly sprayed on powdery or particulate trioxane uniformly. This addition method is advantageous in that the effect of preventing caking or adhesion of the composition can be sufficiently exerted with a smaller amount added of the silicone oil or liquid paraffin and a homogeneous composition can be easily prepared.

When a powdery silicone resin or solid paraffin is used, the silicone resin or solid paraffin can be stirred and mixed with powdery or particulate trioxane.

Other additives such as a perfume and a stabilizer can be added to the composition of the present invention according to need.

The trioxane composition of the present invention is characterized in that caking in a vessel and bridging in a hopper are not caused during storage, custody and transportation of the powdery or particulate composition. Accordingly, the composition can be handled very easily.

Furthermore, the trioxane composition of the present invention does not adhere to the wall of a molding machine and is easily molded from the powdery or particulate state composition is very easy, and therefore, its molding efficiency can be greatly increased.

For better illustration, the present invention will now be described with reference to the following examples.

EXAMPLE 1

In a polyethylene bag having a size of 45 cm × 60 cm, 3 kg of a trioxane flake was thinly spread, and a predetermined amount of octamethylcyclotetrasiloxane (Silicone Oil TSF 404 supplied by Toshiba Silicone; viscosity of 2.4 cSt as measured at 25° C.) was sprayed on the flake to form a composition.

A polyethylene bag having a size of 30 cm × 30 cm was filled with 2.5 kg of the so-prepared composition and was sealed and allowed to stand still at room temperature for 2 days or 7 days. The composition was pressed by a hand from above the polyethylene bag to evaluate the caking property according to the following three stages:

A: easily collapsed by pressing
B: collapsed by strong pressing
C the composition was caked and only the strongly pressed portion was concaved The obtained results are shown in Table 1.

EXAMPLES 2 THROUGH 4

The procedures of Example 1 were repeated in the same manner except that a predetermined amount of a linear methylphenylsilicone oil (Silicone Oil TSF 431 supplied by Toshiba Silicone; viscosity of 100 cSt as measured at 25° C.), a liquid paraffin or n-tetradecane was used instead of Silicone Oil TSF404, and the caking property was evaluated. The obtained results are shown in Table 1.

EXAMPLE 5

A polyethylene bag having a size of 45 cm × 60 cm was filled with 3 kg of a trioxane flake and a predetermined amount of a silicone resin (Tospearl 120 supplied by Toshiba Silicone; average particle size of 2 um) was added and mixed sufficiently with the flake to form a trioxane/silicone resin composition. The caking property of the obtained composition was evaluated in the same manner as described in Example 1. The obtained results are shown in Table 1.

COMPARATIVE EXAMPLE 1

The procedures of Example 1 were repeated in the same manner by using the trioxane alone. The obtained results are shown in Table 1.

TABLE 1

| | Additive | | Caking Property | |
|---|---|---|---|---|
| | Kind | Amount (%) by weight | 2 days | 7 days |
| Example 1 | Silicone Oil TSF404 | 0.1 | A | B |
| Example 2 | Silicone Oil TSF431 | 0.05 | A | A |
| Example 3 | liquid paraffin | 0.1 | A | A |
| Example 4 | n-tetradecane | 0.05 | A | B |
| Example 5 | silicone resin | 0.1 | A | A |
| Comparative Example 1 | not added | | B | C |

EXAMPLE 6 THROUGH 10

A composition was prepared by spraying a predetermined amount of Silicone Oil TSF404, decamethylcyclopentasiloxane (Silicone Oil TSF405 supplied by Toshiba Silicone; viscosity of 4.0 cSt as measured at 25° C.), Silicone Oil TSF 431, a liquid paraffin or n-pentadecane on a trioxane flake. Then, 200 g of the composition was lightly packed in a plugged stainless steel funnel for powders, which had a dropping opening diameter of 25 mm and a slope angle of 40° to the horizon, and the packed composition was allowed to stand still for 1 hour. The plug of the dropping opening was removed and the time required for the whole composition to slip down from the opening completely was measured. When falling of the composition was stopped by bridging or the like, the dropping opening of the funnel was lightly tapped. The obtained results are shown in Table 2.

COMPARATIVE EXAMPLE 2

The procedures of Examples 6 through 10 were repeated in the same manner by using the trioxane flake alone. The obtained results are shown in Table 2.

TABLE 2

| | Additive | | Required Time (seconds) | Frequency (times) of Tapping |
|---|---|---|---|---|
| | Kind | Amount (%) by weight | | |
| Example 6 | Silicone Oil TSF404 | 0.2 | 5 | 2 |
| Example 7 | Silicone Oil TSF405 | 0.1 | 9 | 4 |
| Example 8 | Silicone Oil TSF431 | 0.1 | 5 | 2 |
| Example 9 | liquid paraffin | 0.05 | 10 | 5 |
| Example 10 | n-pentadecane | 0.1 | 11 | 6 |
| Comparative Example 2 | not added | | 33 | 25 |

EXAMPLES 11 THROUGH 15

A predetermined amount of Silicone Oil TSF405, a higher fatty acid-modified silicone oil (Silicone Oil TSF410 supplied by Toshiba Silicone; viscosity of 30 cSt as measured at 25° C.), Silicone Oil TSF431, a liquid paraffin or n-hexadecane was added to trioxane melted at 65° C. and the mixture was externally cooled to 25° C. with strong stirring by a kneader to obtain a powdery composition. The composition was compression-molded under a pressure of 150 kg/cm$^2$ for 1 minute by a tablet-forming machine to obtain tablets having a diameter of 20 mm and a thickness of 5 mm. Bleeding of the silicone oil or liquid paraffin on the tablet surface was not observed.

The adhesion of the composition was evaluated according to the following scale:

+: the composition adhered to the mortar or pestle of the molding machine and withdrawal of stablets from the molding machine was difficult −: the composition did not adhere to the mortar or pestle, withdrawal of tablets from the molding machine was easy The obtained results are shown in Table 3.

COMPARATIVE EXAMPLE 3

In the same manner as described in Example 11, a trioxane flake was compression-molded under a pressure of 150 kg/cm$^2$ for 1 minute by a tablet-forming machine to obtain tablets having a diameter of 20 mm and a thickness of 5 mm. The obtained results are shown in Table 3.

TABLE 3

| | Additive | | Adhesion |
|---|---|---|---|
| | kind | amount (%) by weight | |
| Example 11 | Silicone Oil TSF405 | 0.05 | − |
| Example 12 | Silicone Oil TSF410 | 0.1 | − |
| Example 13 | Silicone Oil TSF431 | 0.2 | − |
| Example 14 | liquid | 0.05 | |

TABLE 3-continued

| | Additive | | |
|---|---|---|---|
| | kind | amount (%) by weight | Adhesion |
| | paraffin | | |
| Example 15 | n-hexadecane | 0.05 | — |
| Comparative Example 3 | not added | | + |

EXAMPLE 16

In the process for the continuous preparation of flaky trioxane from molten trioxane, a spray nozzle was arranged in a flake delivery path downstream of a flaker. Silicone Oil TSF 405 was supplied from the spray nozzle in an amount of 0.1% by weight based on the flaky trioxane, whereby a flaky composition was continuously obtained.

A polyethylene bag having a size of 45 cm x 60 cm was filled with 10 kg of the obtained composition and was then sealed and allowed to stand still in a warehouse at an ambient temperature of 10 to 23° C.

After 60 days, the composition was massive, but the mass was easily collapsed by pressing from the outside of the bag and the whole composition could be made flaky again.

COMPARATIVE EXAMPLE 4

The procedures of Example 16 were repeated in the same manner without incorporation of the additive.

After 60 days' standing, trioxane which was initially flaky became massive in the bag. This mass was not collapsed by pressing. Furthermore, when the mass was beaten by a wooden hammer, the mass was collapsed only partially, and it was very difficult to make the entire composition flaky again.

We claim:

1. A 1,3,5,-trioxane composition improved in the adhesion resistance and caking resistance, consisting essentially of 1,3,5,-trioxane and silicone, wherein the silicone is contained in an amount of 0.003 to 1% by weight based on 1,3,5,-trioxane.

2. A trioxane composition as set forth in claim 1, wherein the silicone is a silicone oil having a viscosity of 1 to 10,000 cSt as measured at 25° C.

3. A trioxane composition as set forth in claim 1, wherein the silicone is a linear polydialkylsiloxane, a linear polyalkylarylsiloxane or a cyclicpolydialkylsiloxane.

4. A trioxane composition as set forth in claim 1, wherein the silicone is octamethylcyclotetrasiloxane or decamethylcyclopentasiloxane.

5. A trioxane composition as set forth in claim 1, wherein the silicone is a powdery silicone resin.

6. A trioxane composition as set forth in claim 1, wherein the silicone is contained in an amount of 0.1 to 0.3% by weight based on the trioxane.

7. An insect-proofing agent comprising a trioxane composition set forth in claim 1.

* * * * *